United States Patent
Buchacher et al.

(10) Patent No.: US 7,553,938 B2
(45) Date of Patent: Jun. 30, 2009

(54) METHOD OF PROVIDING A PURIFIED, VIRUS SAFE ANTIBODY PREPARATION

(75) Inventors: Andrea Buchacher, Vienna (AT); Günther Iberer, Vösendorf (AT); Jürgen Römisch, Gramatneusiedl (AT)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 10/590,900

(22) PCT Filed: Feb. 25, 2005

(86) PCT No.: PCT/EP2005/050812

§ 371 (c)(1),
(2), (4) Date: Feb. 20, 2007

(87) PCT Pub. No.: WO2005/082937

PCT Pub. Date: Sep. 9, 2005

(65) Prior Publication Data

US 2007/0173638 A1    Jul. 26, 2007

Related U.S. Application Data

(60) Provisional application No. 60/548,107, filed on Feb. 27, 2004.

(51) Int. Cl.
*A61K 39/395* (2006.01)
*C07K 1/18* (2006.01)
*C07K 1/34* (2006.01)

(52) U.S. Cl. ............... 530/390.1; 424/176.1; 424/177.1; 530/390.5; 530/414; 530/416; 530/419

(58) Field of Classification Search ........................ None
See application file for complete search history.

(56) References Cited

U.S. PATENT DOCUMENTS

| 6,307,028 B1 * | 10/2001 | Lebing et al. | 530/390.1 |
| 7,138,120 B2 * | 11/2006 | Laursen et al. | 424/176.1 |
| 2007/0244305 A1 * | 10/2007 | Parkkinen | 530/390.1 |

FOREIGN PATENT DOCUMENTS

| EP | 0 374 625 A | | 6/1990 |
| EP | 0893450 | * | 1/1999 |
| WO | WO 2005/073252 | * | 8/2005 |

OTHER PUBLICATIONS

Steinbuch, M et al., "Isolement de l'immunoglubuline lgG du plasma humain a l'aide de l'acide caprylique," Rev. Franc. Etudes Clin. et Biol., vol. 14, 1969, pp. 1054-1058 (Abstr. Only Considered).*
Lundblad, J. L et al., "Inactivation of Lipid-Enveloped Viruses in Proteins by Caprylate," Vox Sanguinis, S karger AG, Basel, CH, vol. 60, No. 2, 1991, s. 75-81.*
Lebing, W. et al., "Properties of a new intravenous immunoglobulin (IGIV-C, 10pc) produced by virus inactivation with caprylate and column chromatography," Vox Sanguinis, vol. 84, 2003, pp. 193-201.
Trejo, S. R. et al., "Evaluation of virus and prion reduction in a new intravenous immunoglobulin manufacturing process," Vox Sanguinis, vol. 84, 2003, pp. 176-187.

* cited by examiner

*Primary Examiner*—David A Saunders
(74) *Attorney, Agent, or Firm*—Venable LLP; Ann S. Hobbs; Matthew E. Kelley

(57) ABSTRACT

A method of preparing a purified, virus inactivated and virus safe antibody preparation from a starting solution comprising antibodies and contaminants, the method comprising the steps of: (a) adjusting the pH of the starting solution to about 4.6 to about 4.95 in particular to about 4.8 to about 4.95 to produce an intermediate solution; (b) adding caprylate and/or heptanoate ions to the intermediate solution and maintaining the pH at about 4.6 to about 4.95 in particular pH at about 4.8 to about 4.95, whereby a precipitate is formed and the antibodies are essentially present in the supernatant; (c) incubating the supernatant solution under conditions of caprylate and/or heptanoate ion concentration, time, pH and temperature optionally concentrating and diafiltrating the filtrated solution before pH adjustment; (d) applying the filtered solution with a least one anion exchange resin and optionally with two different anion exchange resins under conditions that allow binding of contaminants to the resin while not allowing significant binding' of the antibodies to the resin, wherein a purified, virus inactivated and virus safe antibody preparation is produced.

26 Claims, 2 Drawing Sheets

Figure 1:
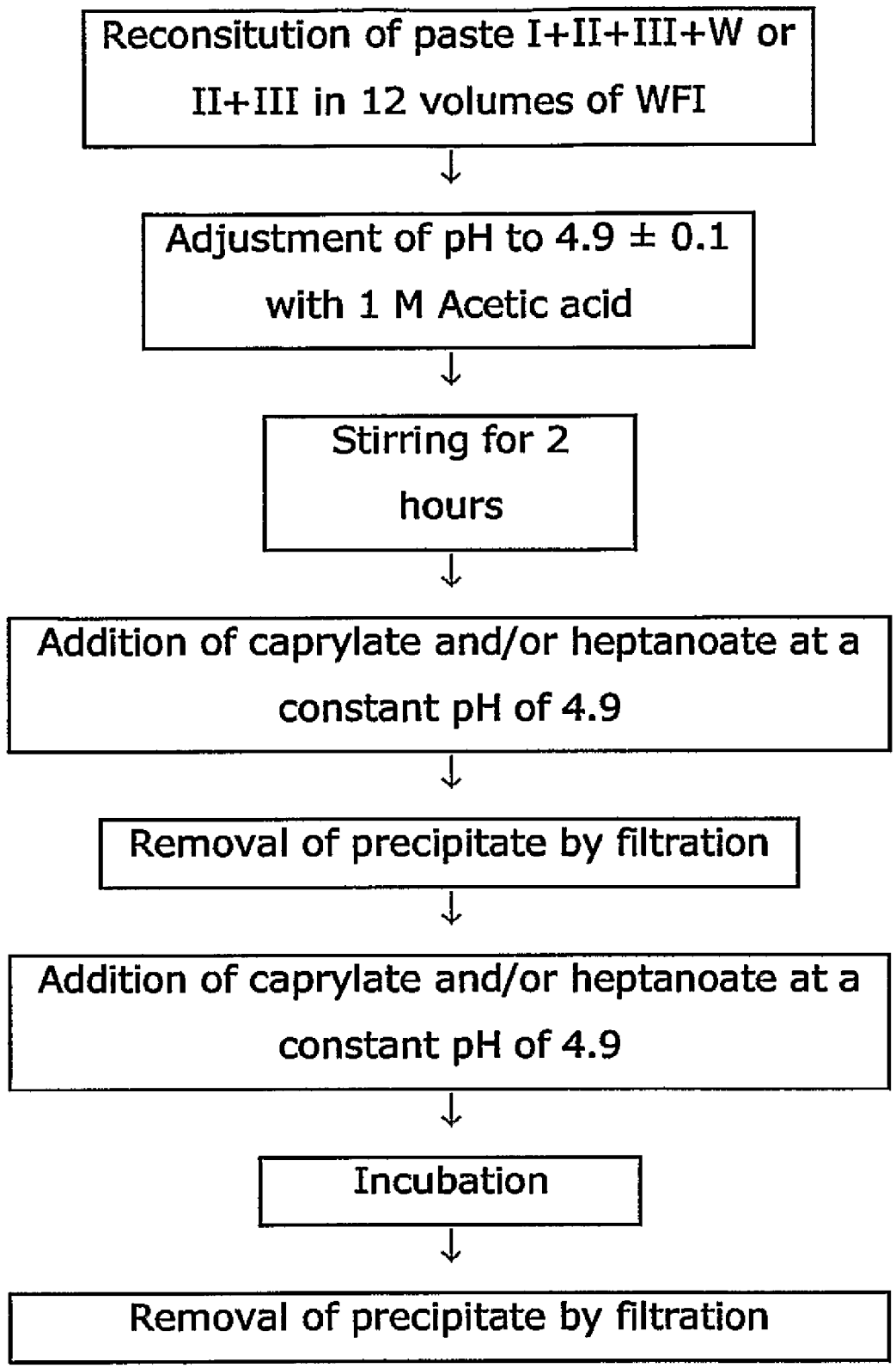

All boxes with an asterisk are optional process steps.

METHOD OF PROVIDING A PURIFIED, VIRUS SAFE ANTIBODY PREPARATION

The present invention concerns a method of preparing a purified, virus safe antibody preparation from a starting solution comprising antibodies and contaminants. It describes a purification process of gamma-globulins from human plasma and other sources. Virus inactivation and removal steps are included in the manufacturing process described here.

Precipitation and Resulting Virus Removal/Inactivation

In the 1940s Cohn et al. introduced the cold ethanol fractionation of human plasma. Several variations of this scheme came up to increase the purity and/or yield of the different intermediates. In Cohn fractionation some steps were identified to contribute efficiently to virus inactivation and removal. In the IgG process especially the separation of Cohn I+III fraction is very effective in this respect. Some sensitive viruses (mainly enveloped viruses) are destroyed by low pH and EtOH presence and a great part of enveloped and non-enveloped viruses is removed by partitioning in the precipitate I+III which is usually discarded.

In the 1960s it was shown that short fatty acids (C6-C12) form insoluble complexes with $\alpha$- and $\beta$-globulins whereas $\gamma$-globulins are not as readily precipitated (Chanutin et al., 1960). Steinbruch et al (1996) described a purification process for IgG with caprylate (i.e. octanoate, a C8-saturated fatty acid) as precipitating agent. Non-immunoglobulins were precipitated from human plasma after dilution with an acetate buffer to reach a final pH of 4.8. After addition of caprylate under vigorous stirring an IgG enriched solution was obtained. The purity and yield depended on the amount of caprylic acid, the pH, the molarity of the buffer and the dilution factor. Steinbruch et al. also stated that it is advantageous to add the effective amount of caprylate in two steps with the removal of the precipitates inbetween. Non-enveloped and enveloped viruses are removed by partitioning in the precipitate of the non IgG proteins as is the case for the separation of the I+III fraction.

Chromatography

Several patents describe the purification of IgG solution in the so called negative mode; IgG runs through without binding (only in traces) whereas the majority of the non-IgG fraction proteins bind to the anionic ligands (Bertolini et al. 1998, WO-A-98/05686; Lebing 1999, U.S. Pat. No. 5,886, 154; Friesen et al., 1986, CA 1201063). The combination of caprylate precipitation followed by ion-exchange chromatography for the purification of IgG was described in many publications. One of the first was written by Steinbuch et al. (1969). He described the further purification of IgG after precipitation of caprylate with DEAE-cellulose. The recent publication by Lebing et al. (2003) describes two anion-exchange columns used in series for the removal of IgM, IgA, albumin and other impurities. Lebing et al. combined both caprylate mediated effects, namely the essential reduction of non-IgG proteins by precipitation, thereby using the virus partitioning, and the enveloped virus inactivation properties of the fatty acid in a separate incubation step. The importance of the so-called "pH-swing" Lebing et al. (2003), starting from the reconstitution of an IgG containing paste/precipitate at pH 4.2 and the subsequent addition of caprylate upon adjusting the pH 5.2 is stressed to be essential for the IgG enriching procedure, thus needed to effectively reduce non-IgG proteins. As a few other impurities, like IgA and IgM, as well as the caprylate were subsequently reduced by the mentioned ion exchange chromatography steps.

Surprisingly we found that such pH-shift as outlined above and described by Lebing et al. is not needed to achieve a significant purification effect upon caprylate addition and removal of the resulting precipitate. Instead, upon keeping the pH constant at pH 4.6 to 4.95 during the entire process of paste reconstitution and caprylate incubation and precipitate removal, an effective IgG enrichment is achieved. Also the amount of impurities especially albumin is reduced more efficiently by keeping the pH constant in the range of 4.8 to 4.95. At the same time viruses are removed. Afterwards residual impurities and caprylate are separated by ion exchange steps.

Classical Virus Inactivation

The solvent detergent and pH 4 treatments are well known methods and widely used for immunoglobulins. The SD treatment is normally introduced into these processes due to its superiority in terms of inactivation of enveloped viruses (Biesert L. Clinical and Experimental Rheumatology 1996; 14: 47). Both enveloped and non-enveloped viruses are affected by the exposure to low pH, although enveloped viruses are more affected than the non-enveloped (Biesert. Clinical and Experimental Rheumatology 1996; 14: 47, Bos et al. Biologicals 1998; 26: 267, In Seop et al. J Microbiol Biotechnol 2001; 11: 619).

In EP-A-0 525 502 the combination of solvent detergent and pH 4 incubation as virus inactivation steps are described.

Virus Filtration

IgG solutions are filtered through membranes of very small pore size (typically 15 to 50 nm) under conditions that retain viruses by a mechanism largely based on size exclusion (Burnouf and Radosevich. Haemophilia 2003; 9: 24) to increase the virus safety. Also depth filters designed to retain viruses by ion exchange adsorption are used for filtration of immunoglobulins.

SUMMARY OF THE INVENTION

The invention describes a purification process of IgG with an increased yield and shorter process time compared to the classical Cohn-Oncly fractionation process. IgG is reconstituted in buffer at an acidic pH range from 4.60 to 4.95, preferentially 4.9. Non-IgG proteins are separated by two incubation steps with caprylate at a concentration range from 10 to 30 mM caprylate, preferably 20 mM.

For effective inactivation of enveloped viruses, an incubation known as solvent detergent treatment with Triton X-100, Tween 80 etc. and TNBP, can be added to increase the virus inactivation capacity of the entire process. A virus removal by filtration, i.p. by the so-called nanofiltration or charged depth filters may be added to the virus removal procedures. Furthermore, UVC treatment may be performed also in combination with the treatments mentioned before. Such treatments are described e.g. in EP-A-0 840 624 or EP-A-0 422 007.

Furthermore, caprylate/caprylic acid can be combined with or replaced by heptanoate/heptanoic acid to perform the aforementioned precipitation and incubation process steps.

The product obtainable by the method of the invention is virus inactivated. Prions are inactivated/removed as well due to the caprylate treatment.

Figure 2:
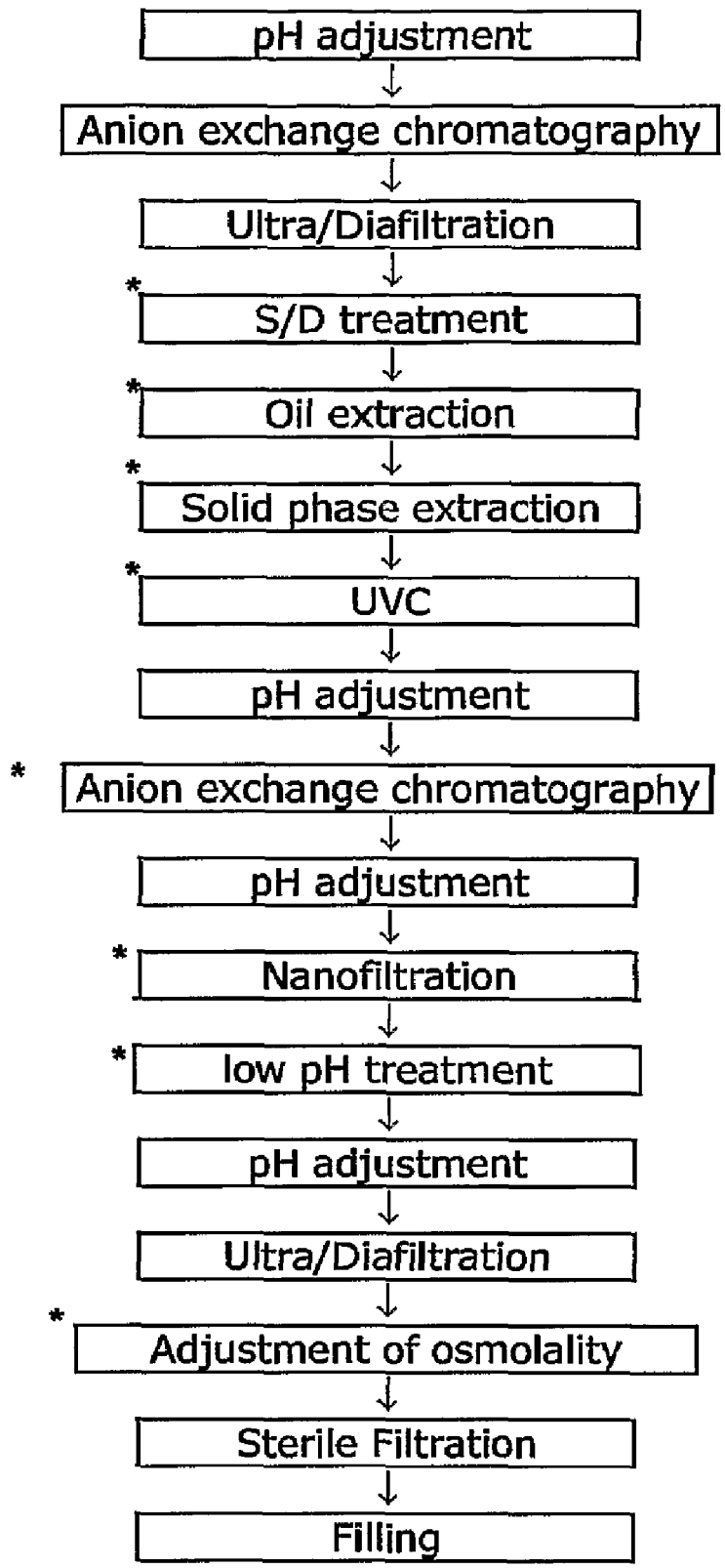

FIGS. 1 and 2 depict a flow-chart of particular embodiments of the process of the invention.

DETAILED DESCRIPTION OF THE INVENTION

The invention concerns a method of preparing a purified, virus inactivated and virus safe antibody preparation from a starting solution comprising antibodies and contaminants, the method comprising the steps of:

(a) adjusting the pH of the starting solution to about 4.6 to about 4.95 in particular to about 4.8 to about 4.95 to produce an intermediate solution;
(b) adding caprylate and/or heptanoate ions to the intermediate solution and maintaining the pH at about 4.6 to about 4.95 in particular at about 4.8 to about 4.95 whereby a precipitate is formed and the antibodies are essentially present in the supernatant;
(c) incubating the supernatant solution under conditions of caprylate and/or heptanoate ion concentration, time, pH and temperature; optionally concentrating and diafiltrating the filtered solution before pH adjustment;
(d) applying the filtered solution with at least one anion exchange resin and optionally with two different anion exchange resins under conditions that allow binding of contaminants to the resin while not allowing significant binding of the antibodies to the resin, wherein a purified, virus inactivated and virus safe antibody preparation is produced.

In one embodiment of the invention the virus inactivated solution is contacted in step (d) with the at least one anion exchange resin at pH of from about 5.0 to 5.2. If two anion exchanger chromatographies are performed, the second chromatography can be performed at a pH range of from 6.7 to 6.9. Optionally steps (b) and (c) may be repeated at least one time. The treatment with caprylate at a pH 4.9 leads to a significant depletion of unwanted proteins.

Typically, the starting solution comprises plasma-derived antibodies.

It may be advantageous to contact in step (d) the inactivated solution with two different anion exchange resins under conditions such that contaminants are selectively bound to the resins while the antibodies are not significantly bound to the resins.

Preferably, the antibodies are of the immunoglobulin G-type.

Between the two anion-exchange chromatography (AEX) steps the pH may be changed in particular to 6.8±0.1. The AEX flow through may be concentrated to 60 to 90 mg/ml and diafiltrated against e.g. phosphate buffer. In another embodiment of the method of the invention the flow through of the first AEX is solvent detergent treated, preferably by Triton X-100 and TnBP, preferably at concentrations of 1% Triton X-100 and 0.3% TnBP for 4.5 to 8 hours to inactivate lipid coated viruses. The method is known as solvent-detergent-treatment and disclosed in EP-A-0 131 740 (incorporated by reference). According to the invention, the detergents of the incubation mixture are in particular removed by solid and liquid phase extraction. After solid phase extraction the pH of the solution is adjusted to 6.7 to 6.9. The combination of the S/D treatment and caprylate virus inactivation leads to a safer product.

The solution thus adjusted can be applied to the second AEX column where the AEX flow through may be pH adjusted to e.g. 3.5 to 4.5, in particular 4.0±0.1. According to the invention the pH adjusted IgG solution is contacted by a virus filter. This optional step leads in combination with the caprylate treatment to more virus safety.

The IgG solution can also be incubated at 37° C.±1 for at least 24 hours. In order to improve the virus safety of the antibody product UV-C treatment may be combined with the caprylate treatment of the antibody containing fraction. The inactivation methods alone or in combination such as treatment with TnBP, UV-C treatment, virus filtration or heating can be combined with the process of the invention.

The method according to the invention may be combined with methods for removal or inactivation of prions e.g. filtration or adsorption methods or chromatographic methods as disclosed in the prior art e.g. EP-A-0 954 528, Trejo, S. R. et al., Vox Sanguinis, (2003) 84, 176-187. The IgG solution obtained according to the invention is concentrated due to the intended therapeutical use, typically to concentrations of 5 or 10% and the osmolarity of the concentrate is adjusted to 200 to 400 mOsmol/kg by an appropriate additive. However, any other value is possible as long as pharmaceutically acceptable. Such additives are well known to the expert and include but are not limited to sugars, sugar alcohols and amino acids. The IgG solution may be pH adjusted to 3.5 to 6.0, in particular 4.0 to 5.5. Finally, the IgG solution is sterile filtered and filled in glass bottles or plastic containers. Alternatively, the flow through after the first or second AEX step is applied to nanofilters to achieve an even safer product.

The process of invention is described in more detail, preferentially performed as outlined:

As starting material human plasma fraction I+II+III or fraction II+III was used. These fractions were produced as described by Cohn et al. (1946). The adjustment of the pH during the process was done with 1 M acetic acid, 0.1 M NaOH or 0.3 M HCl. Caprylate was added as a 1 M sodium caprylate stock solution. This stock solution was prepared by dissolving 166 g of sodium caprylate in 1 liter of water for injections (WFI) and stirring until total dissolution of sodium caprylate.

Examplary for the SD treatment Triton X-100 and TnBP were used. For the removal of the SD reagents vegetable oil such as soy bean oil or castor oil were used.

All reagents were USP grade or better.

Quantitative size exclusion chromatography and ELISA were used to determine the IgG concentration. Analytical HPLC was done with an Agilent HPLC System with Toso-Haas G3000SW column.

A schematic drawing of the process is shown in FIG. 1. The process starts with the dissolving of the IgG precipitate, called paste, in purified water. Usually the higher the volume of water to reconstitute the paste the higher is the yield of IgG. The pH of the solution is adjusted to 4.60 to 4.95, preferably to 4.90 with 1 M acetic acid. The solution is stirred for several hours to get as much IgG as possible in solution. Afterwards caprylate is added as a 1 M stock solution up to concentrations between 10 and 30 mM, preferably 20 mM caprylate. The pH during the addition of caprylate is kept constant between 4.80 and 4.95, preferably at 4.90. During the incubation of the IgG solution with caprylate non-IgG proteins and lipids precipitate. The formed precipitate is removed by filtration from the IgG solution. After the first precipitation step some impurities remain in the IgG solution. Therefore a second caprylate treatment is necessary. Similar to the first step the caprylate is added as 1 M stock solution up to a concentration of approximately 20 mM caprylate in solution at a constant pH between 4.80 and 4.95, preferably at 4.9. After the incubation the precipitate is removed by filtration or centrifugation. For a better performance during the filtration filter aid is used. The filtered solution is adjusted to a pH between 5.0 and 5.2, preferably to 5.1 and applied to an anion-exchange column. As an anion exchange column, preferably strong anion exchangers such as Q-Sepharose-FF, Q-Sepharose HP, Q-Sepharose-XL, Source Q 15 or 30 (Amersham Biosience), Q-Thruput, Q-Thruput plus (Sterogene), Macro Prep Q and Macro Prep High Q (Bio-Rad), Q Hyper D (BioSepra) and Poros HQ (PerSeptive Biosystems) were chosen.

The IgG flows through the column under the chosen conditions, whereas some additives/impurities such as caprylate and IgA bind to the resin. The protein solution is loaded onto the column at a ratio of 40 to 120 mg, in particular of 40 to 90 mg protein per ml resin. The obtained flow through is concentrated to a protein concentration of 60 to 90 mg/ml, preferably 70 mg/ml and diafiltrated against 5 volumes of phosphate buffer with a concentration of 5 to 20 mM, preferably 10 mM sodium phosphate. As an optional virus inactivation step the SD treatment can be chosen after the diafiltration. The diafiltrated solution is then virus inactivated using the SD treatment described by Horowitz e.g. in EP-A-0 131 740. As SD reagents TnBP and Triton X-100 were used. After stirring, the solution is incubated up to 8 hours at a temperature between 4 and 10° C. Then a vegetable oil such as soy bean oil or castor oil, preferably castor oil is added to the solution up to a concentration of 3 to 5% (w/w). After the separation of the oily phase from the aqueous phase, the aqueous phase is filtrated. Therefore an appropriate depth filter is used. Examples for these filters are Polysep II (Millipore), Sartofine PP and Sartobran P (Sartorius). The subsequent solid phase extraction is performed in a preferred mode using a hydrophobic support media which are also used in reversed phase chromatography with a gel matrix made of silica, styrene-co-divinyl benzene (SDVB), glycidyl methacrylate-co-ethylene dimethacrylate or polyaromatic.

Examples for these media are µBondapak (Waters), Amberchrom CG-161 M and S, Amberchrom CG-070 (Tosoh Biosep), PLRP-S (Polymer Laboratories), RPC-1 and Toyopearl Hexyl 650C (Tosoh Biosep), Source 15 RPC (Amersham Biosiences), UiChroprep Si60(Merck), Chromabond Sorbent HR-P and EASY (Machery-Nagel), ProntoSORB SPE (Bischoff Chrom.). The protein solution is loaded onto the column in a ratio of 0.5 to 1.5 mg/ml dry resin. The flow through of the solid phase extraction (or chromatography step, respectively) is UVC treated and then adjusted to a pH between 6.7 and 6.9, preferably 6.8 by the addition of 0.1 M NaOH at a temperature between 4 and 10° C. Afterwards the IgG solution is applied to a second anion exchange column. The IgG flows unretained through the column, whereas impurities and polymers bind to the column. As an anion exchange column, preferably strong anion exchangers such as Q-Sepharose-FF, Q-Sepharose HP, Q-Sepharose-XL, Source Q 15 or 30 (Amersham Biosience), Q-Thruput, Q-Thruput plus (Sterogene), Macro Prep Q and Macro Prep High Q (Bio-Rad), Q Hyper D (BioSepra) and Poros HQ (PerSeptive Biosystems) were chosen. The column is equilibrated with a 10 mM sodium phosphate buffer. After the application of the IgG solution the column is washed with equilibration buffer to obtain all non bound IgG from the column. The protein solution is loaded onto the column at a ratio of 120 to 300 mg protein/ml resin. The collected IgG solution is adjusted to a pH between 3.9 and 4.1, preferably 4.0 with 0.3 M HCl at a temperature between 4 and 10° C. Then the solution is sterile filtered and stored at 37° C. for at least 24 hours. Subsequent to the low pH treatment the pH of the solution is adjusted to 4.7 with 0.1 M NaOH at a temperature between 4 and 10° C. As an additional virus reduction step appropriate virus filters can be used. For virus filtration the IgG solution was filtered through a 0.1 µm filter followed by virus filters with a pore size between 200 and 15 nm. Examples for these filters are DVD, DV 50, DV 20 (Pall), Viresolve NFP, Viresolve NFR (Millipore), Planova 75, 35, 20, 15N (Asahi Kasei Pharma). Also a charged depth filter like Zeta Plus VR (Cuno) can be used. This filtration step can also be applied after pH 4 incubation. Preferably this step will be implemented in the process before the low pH treatment. The highly purified IgG solution is diafiltered and concentrated to the final formulation values. As final concentrations for a liquid formulation protein concentrations of 5 or 10% (w/v) were chosen. After the concentration the osmolarity is adjusted to be compatible for intravenous injection by an appropriate additive. Sugars, sugar alcohols and amino acids can be used. The pH is checked again and adjusted to 4.5 to 5.0, preferable to 4.7. Subsequently another sterile filtration is carried out and the solution is filled into infusion bottles.

The following examples explain the process of invention in more detail:

EXAMPLE 1

The Cohn fraction I+II+III or II+III was dissolved in 12 volumes of water, the pH was adjusted to 4.9 with 1 M acetic acid and the solution was stirred for up to 5 hours until most of the IgG was dissolved at a temperature of 2 to 8° C. Afterwards caprylate was added as a 1 M sodium caprylate stock solution to the IgG solution up to a concentration of 20 mM caprylate while keeping the pH constant at 4.9 by adding 1 M Acetic acid. This solution was stirred for one hour. Lipids and impurities precipitated under these conditions and were removed by filtration. Afterwards caprylate was added again to the solution up to a concentration of 20 mM in solution upon keeping the pH constant at 4.9. Again a precipitate was generated and removed by filtration. A clear solution was obtained after the filtration. The solution was adjusted to a pH of 5.1 with 0.1 M NaOH at a temperature of 7±3° C. and applied to Source Q 30 column. The IgG solution flew through the column whereas the impurities and caprylate were bound to the column. The collected IgG solution was concentrated to a protein concentration of 70 mg/ml and diafiltered against 5 volumes of a phosphate buffer pH 5.1. Subsequently, 0.3% (w/w) of TnBP and 1% (w/w) of Triton X-100 were added to the solution, followed by vigorous stirring. After at least 4.5 hours of stirring at 7±3° C., 5% (w/w) of castor oil is added. The oil extraction was performed at room temperature. The oily and aqueous phases were separated and the aqueous phase was filtrated with a Millipore Opticap Polysep filter. The filtered solution was applied to a column filled with a reversed phase matrix named µBondapak (Waters). Then the solution was adjusted to pH of 6.8 with 0.1 M NaOH at a temperature of 7±3° C. and applied to a strong anion exchanger, namely Q-Sepharose-XL. The IgG ran through the column whereas the impurities were bound to the column. The pH of the collected IgG solution was adjusted to 4.7 with 0.1 M NaOH at a temperature of 7±3° C. Again an ultrafiltration was carried out to adjust the protein concentration to the final concentration of 50 or 100 mg/ml, followed by the addition of maltose to a concentration range from 2 to 10% (weight), preferably 8% or glycine in a concentration range from 0.1 to 0.5 M in particular 0.1 to 0.3, preferably 0.3 M in particular 0.2. Subsequently to the following sterile filtration, the solution was filled into sterilized and siliconized infusion bottles with different volumes (50, 100, 200 ml). The bottles were sealed by stoppers.

EXAMPLE 2

This example in particular differs from example 1 by the implementation of a pH 4 incubation step. The Cohn fraction I+II+III or II+III was dissolved in 12 volumes of water, the pH was adjusted to 4.9 with 1 M acetic acid and the solution was stirred for up to 5 hours until most of the IgG was dissolved at a temperature of 2 to 8° C. Afterwards caprylate was added as a 1 M sodium caprylate stock solution to the IgG solution up to a concentration of 20 mM caprylate in solution and the pH was kept constant at 4.9 by adding 1 M acetic acid. This solution was stirred for one hour. Lipids and impurities precipitated under this circumstances and were removed by filtration. Afterwards caprylate was added again to the solution up to a concentration of 20 mM upon keeping the pH constant at 4.9. Again the formed precipitate was removed by filtration. A clear solution was obtained after the filtration. The collected IgG solution was concentrated to a protein concentration of 70 mg/ml and diafiltered against 5 volumes of a phosphate buffer pH 5.1. The solution was adjusted to a pH of 5.1 with 0.1 M NaOH at a temperature of 7±3° C. and applied to the strong anion exchanger Q-Sepharose-XL. The IgG flew through the column whereas the impurities and caprylate were bound to the column. Subsequently, 0.3% (w/w) of TnBP and 1% (w/w) of Triton X-100 were added to the solution, followed by vigorous stirring. After at least 4.5 hours of stirring at 4 to 10° C., 5% (w/w) of castor oil was added. The oil extraction was performed at room temperature. The oily and aqueous phases were separated and the aqueous phase was filtrated with a Millipore Opticap Polysep filter. The filtered solution was applied to a column filled with Amberchrom CG-161M. Then the solution was adjusted to pH of 6.8 with 0.1 M NaOH at a temperature of 7±3° C. and applied to the strong anion exchanger Q-Hyper D. The IgG flew through the column whereas the impurities were bound to the column. The pH of the collected IgG solution was adjusted to 4.0 with 0.3 M HCl at a temperature of 7±3° C. The solution was sterile filtrated and stored at 37±3° C. for at least 24 hours. Afterwards the pH of the solution was adjusted to 4.7 with 0.1 M NaOH at a temperature of 7±3° C. Again an ultrafiltration was carried out to adjust the protein concentration to the final concentration of 50 or 100 mg/ml to be obtained after formulation with maltose or glycine. Subsequently to the following sterile filtration, the solution was filled into sterilized and siliconized infusion bottles with different volumes (50, 100, 200 ml). The bottles were sealed by stoppers.

EXAMPLE 3

This example in particular differs from the former samples by concentration the IgG solution to 70 mg/ml protein concentration before the first AEX step and by implementation of a nanofiltration step.

The Cohn fraction I+II+III or II+III was dissolved in 12 volumes of water, the pH was adjusted to 4.9 with 1 M acetic acid and the solution was stirred for up to 5 hours until most of the IgG is dissolved at a temperature of 2 to 8° C. Afterwards caprylate was added as a 1 M sodium caprylate stock solution to the solution up to a concentration of 20 mM caprylate in solution and the pH was kept constant at 4.9 by adding 1 M acetic acid. This solution was stirred for one hour. Lipids and impurities precipitate under these conditions and were removed with filtration. Afterwards caprylate was added again to the solution up to a concentration of 20 mM upon keeping the pH constant at 4.9. Again a precipitate was generated and removed by filtration. A clear solution was obtained after the filtration. The collected IgG solution was concentrated to a protein concentration of 70 mg/ml and diafiltered against 5 volumes of a phosphate buffer pH 5.1. The solution was adjusted to a pH of 5.1 with 0.1 M NaOH at a temperature of 7±3° C. and applied to a strong anion exchanger. The IgG flew through the column whereas the impurities and caprylate were bound to the column. Then the solution was adjusted to pH of 6.8 with 0.1 M NaOH at a temperature of 7±3° C. and applied to a second strong anion exchanger. The IgG passed through the column whereas the impurities were bound to the column. The pH of the collected IgG solution was adjusted to 4.0 with 0.3 M HCl at a temperature of 7±3° C. The solution was filtrated through a 0.1 pm filter, afterwards a cascade of PALL filters namely PALL DVD, DV 50 and DV 20 with a pore sizes starting down to 20 nm were used for nanofiltration. The nanofiltered solution is stored at 37±3° C. for at least 24 hours. Afterwards the pH of the solution was adjusted to 4.7 with 0.1 M NaOH at a temperature of 7±3° C. Again an ultrafiltration was carried out to adjust the protein concentration to the final concentration of 50 or 100 mg/ml to be obtained after formulation with maltose or glycine. Subsequently to the following sterile filtration, the solution was filled into sterilized and siliconized infusion bottles with different volumes (50, 100, 200 ml). The bottles were sealed by stoppers.

COMPARATIVE EXAMPLES

Method of the Invention

Approx. 310 g Fraction I+II+III (including filter aids) are reconstituted in 12 volumes WFI calculated from the theoretical weight of fraction I+II+III without filter aids. The solution is stirred for 1 hour at 5° C. Then pH is adjusted to 4.9±0.1 (ca. 950 g). Reconstitution is continued for 2 hours at 5° C. Then the sample "reconstituted Fraction I+II+III" is drawn. An 1 molar caprylate solution is added to reach a concentration of 20 mM. pH is kept constant at 4.9. The solution is incubated for 1 hour at 5° C. The solution is filtrated over a depth filter and a paper sheet at 5° C. (ca. 1050 g). The filter is postwashed with a 10 mM sodium chloride solution. The filtrate is warmed to 25° C., the 1 molar caprylate is added to reach an additional 10 mM concentration. The solution is incubated for 1 hour at 25° C. The solution is centrifuged and the supernatant is filtrated over a filter (1110 g) having a pore size of 1 μm and 0.5 μm. The sample "after caprylate" is drawn.

According to EP 0 893 450

Approx. 310 g Fraction I+II+III (including filter aids) are reconstituted in 7 volumes WFI calculated from the theoretical weight of fraction I+II+III without filter aids. The solution is stirred for 1 hour at 5° C. The pH is adjusted to 4.1±0.1. Reconstitution is continued for 2 hours at 5° C. Then the sample "rec. Fr. I+II+III" is drawn. A 1 molar caprylate solution is added to reach a concentration of 20 mM. The pH changes to 4.9 upon addition of caprylate and is adjusted to 5.1. The solution is incubated for 1 hour at 5° C. The solution is filtrated over a depth filter and a paper sheet at 5° C. The filter is postwashed with a 10 mM sodium chloride solution (ca. 1050 g). The filtrate is warmed to 25° C., the 1 molar caprylate is added to reach an additional 10 mMolar concentration. The solution is incubated for 1 hour at 25° C. The solution is centrifuged and the supernatant is filtrated over a 0.45 μm filter (ca. 1110 g). The sample "after caprylate" is drawn.

| Depletion of albumin and IgA | | | |
|---|---|---|---|
| Experiment | Samples | pH 4.9 Invention Albumin [μg/mg IgG] | 5.1 EP 0 893 450 Albumin [μg/mg IgG] |
| 1 | rec. Fr. I + II + III | 27.1 | 32.9 |
|  | after caprylate | 0.2 | 10.2 |
| 2 | rec. Fr. I + II + III | 44.2 | 32.6 |
|  | after caprylate | 0.2 | 2.2 |
| 3 | rec. Fr. I + II + III | 30.2 | 31.2 |
|  | after caprylate | 0.8 | 9.9 |
| 4 | rec. Fr. I + II + III | 22.7 | 33.1 |

-continued

| Depletion of albumin and IgA | | | |
|---|---|---|---|
| after caprylate | | 0.9 | 10.7 |
| average rec. Fr. I + II + III | | 31.1 | 32.5 |
| stand. dev. rec. Fr. I + II + III | | 9.3 | 0.9 |
| average after caprylate | | 0.5 | 8.3 |
| stand. dev. after caprylate | | 0.4 | 4.0 |

| Experiment | Samples | pH 4.9 Invention IgA [µg/mg IgG] | 5.1 EP 0 893 450 IgA [µg/mg IgG] |
|---|---|---|---|
| 1 | rec. Fr. I + II + III | 86 | 106 |
|   | after caprylate | 40.9 | 49.3 |
| 2 | rec. Fr. I + II + III | 74.3 | 120.7 |
|   | after caprylate | 23.7 | 60.5 |
| 3 | rec. Fr. I + II + III | 88.5 | 114 |
|   | after caprylate | 30.8 | 56.9 |
| 4 | rec. Fr. I + II + III | 115.5 | 113.6 |
|   | after caprylate | 34.4 | 51.3 |
|   | average rec. Fr. I + II + III | 91.1 | 113.6 |
|   | stand. dev. rec. Fr. I + II + III | 17.4 | 6.0 |
|   | average after caprylate | 32.5 | 54.5 |
|   | stand. dev. after caprylate | 7.2 | 5.1 |

The invention claimed is:

1. A method of preparing a purified, virus inactivated and virus safe antibody preparation from a starting solution comprising antibodies and contaminants, the method comprising the steps of:
   (a) adjusting the pH of the starting solution to 4.8 to 4.95, to produce an intermediate solution;
   (b) adding caprylate and/or heptanoate ions to the intermediate solution and maintaining the pH at 4.8 to 4.95, whereby a precipitate is formed and the antibodies are essentially present in a supernatant;
   (c) incubating the supernatant under conditions of caprylate and/or heptanoate ion concentration, time, pH and temperature to form a second precipitate and filtering to form a filtered solution;
   (d) applying the filtered solution to a first chromatographic column filled with a first anion exchange resin at a pH from about 5.0 to about 5.2 to perform a first anion-exchange chromatography under conditions that allow binding of contaminants to the resin while not allowing significant binding of the antibodies to the resin, wherein a purified, virus inactivated and virus safe antibody preparation is produced as flow-through.

2. The method of claim 1 further comprising performing a second anion exchange chromatography at a pH range of from 6.7 to 6.9.

3. The method of claim 1 wherein steps (b) and (c) are repeated at least one time.

4. The method of claim 1 wherein the starting solution comprises plasma-derived antibodies.

5. The method of claim 1 further comprising applying the flow-through of the first chromatographic column to a second chromatographic column filled with a second anion exchange resin to perform a second anion-exchange chromatography under conditions that allow binding of contaminants to the resin while not allowing significant binding of the antibodies to the resins.

6. The method of claim 1, wherein the antibodies are immunoglobulin G.

7. The method of claim 5, where the pH is adjusted to 6.7 to 6.9 prior to the second anion-exchange chromatography.

8. The method of claim 1 further comprising concentrating the anion-exchange chromatography flow-through to 60 to 90 mg/ml and diafiltrating the anion-exchange chromatography flow-though against a buffer solution.

9. The method of claim 1 further comprising treating the flow-through of the first anion-exchange chromatography with solvent detergent for 4.5 to 8 hours to inactivate lipid coated viruses.

10. The method of claim 9, further comprising removing the detergents of the incubation mixture by solid and liquid phase extraction.

11. The method of claim 1 further comprising combining the caprylate incubation with one or more of the following- UV-C treatment, heat-treatment, virus filtration, and prion removal or inactivation.

12. The method of claim 10, further comprising adjusting the pH value upon solid phase extraction to 6.7 to 6.9.

13. The method of claim 12, further comprising submitting the flow-through of the first chromatograrhic column to a second chromatograrhic column filled with a second-anion exchange resin to perform a second anion-exchange chromatography under conditions that allow binding of contaminants to the resin while not allowing significant binding of the antibodies to the resins, wherein a purified, virus inactivated and virus safe antibody preparation is produced as a second-anion exchanger flow-through.

14. The method of claim 13, further comprising adjusting the pH value of the second anion-exchanger flow-through to 3.5 to 4.5 to provide a pH-adjusted second anion-exchanger flow-through solution.

15. The method of claim 14, wherein the antibodies are IgG and further comprising contacting the pH-adjusted second anion-exchanger flow-through solution by a virus filter.

16. The method of claim 14, wherein the antibodies are IgG and further comprising contacting the pH-adjusted second anion-exchanger flow-through solution by a nanofilter.

17. The method of claim 14 wherein the antibodies are IgG and further comprising incubating the pH-adjusted second anion-exchanger flow-through solution for at least 24 hours.

18. The method of claim 14, wherein the antibodies are IgG and further comprising concentrating the pH-adjusted second anion-exchanger flow-through solution to 5 or 10% (w/v) to form a concentrate.

19. The method of claim 18, wherein the osmolarity of the concentrate is 200 to 400 mOsmol/kg.

20. The method of claim 19, further comprising adjusting the pH of the IgG concentrate to 3.5 to 6.0.

21. The method of claim 20 further comprising sterile filtering and filling the IgG concentrate in glass bottles or plastic containers.

22. The method of claim 8 wherein the buffer solution is a phosphate buffer solution.

23. The method of claim 9 wherein the solvent detergent is Triton X-100 and TnBP.

24. The method of claim 23 wherein the concentration is 1% Triton and 0.3% TnBP.

25. The method of claim 14, wherein the pH of the second anion-exchanger flow-through is adjusted to 4.0 +/−0.1.

26. The method of claim 17, wherein the incubation temperature is 37° C.+/−1° C.

* * * * *